United States Patent [19]
Muller et al.

[11] Patent Number: 5,658,940
[45] Date of Patent: Aug. 19, 1997

[54] SUCCINIMIDE AND MALEIMIDE CYTOKINE INHIBITORS

[75] Inventors: George W. Muller, Bridgewater; Mary Shire, North Plainfield, both of N.J.

[73] Assignee: Celgene Corporation, Warren, N.J.

[21] Appl. No.: 539,879

[22] Filed: Oct. 6, 1995

[51] Int. Cl.$^6$ .......................... A61K 31/40; C07D 209/48
[52] U.S. Cl. .......................... 514/417; 514/309; 514/339; 514/340; 514/421; 514/425; 546/142; 546/277.1; 546/278.4; 546/278.7; 548/465; 548/479; 548/513; 548/547
[58] Field of Search .......................... 548/546, 465, 548/479, 513, 547; 514/309, 339, 340, 417, 421, 425; 546/142, 277.1, 278.4, 278.7

[56] References Cited

PUBLICATIONS

Chemical Abstracts, vol. 117, Abstract 117:145301t (1992).

*Primary Examiner*—Jacqueline Haley
*Attorney, Agent, or Firm*—Mathews, Collins, Shepherd & Gould, P.A.

[57] ABSTRACT

Novel succinimides and maleimides are inhibitors of tumor necrosis factor α and phosphodiesterase and can be used to combat cachexia, endotoxic shock, retrovirus replication, asthma, and inflammatory conditions. A typical embodiment is methyl 3-(3',4',5',6'-tetrahydrophthalimido)-3-(3",4"-dimethoxyphenyl)propionate.

18 Claims, No Drawings

1

SUCCINIMIDE AND MALEIMIDE CYTOKINE INHIBITORS

BACKGROUND OF THE INVENTION

The present invention relates to a method of reducing levels of TNFα and inhibiting phosphodiesterase in a mammal and to compounds and compositions useful therein.

TNFα, or minor necrosis factor α, is a cytokine which is released primarily by mononuclear phagocytes in response to various immunostimulators. When administered to animals or humans it causes inflammation, fever, cardiovascular effects, hemorrhage, coagulation and acute phase responses similar to those seen during acute infections and shock states.

Excessive or unregulated TNFα production has been implicated in a number of disease conditions. These include endotoxemia and/or toxic shock syndrome (Tracey et al., Nature 330, 662–664 (1987) and Hinshaw et al., Circ. Shock 30, 279–292 (1990)); cachexia (Dezube et al., Lancet, 335(8690), 662 (1990)); and Adult Respiratory Distress Syndrome where TNFα concentrations in excess of 12,000 pg/milliliters have been detected in pulmonary aspirates from ARDS patients (Millar et al., Lancet 2(8665), 712–714 (1989)). Systemic infusion of recombinant TNFα also resulted in changes typically seen in ARDS (Ferrai-Baliviera et al., Arch. Surg. 124(12), 1400–1405 (1989)).

TNFα appears to be involved in bone resorption diseases, including arthritis where it has been determined that when activated, leukocytes will produce a bone-resorbing activity, and data suggests that TNFα contributes to this activity (Bertolini et al., Nature 319, 516–518 (1986) and Johnson et al, Endocrinology 124(3), 1424–1427 (1989)). It has been determined that TNFα stimulates bone resorption and inhibits bone formation in vitro and in vivo through stimulation of osteoclast formation and activation combined with inhibition of osteoblast function. Although TNFα may be involved in many bone resorption diseases, including arthritis, the most compelling link with disease is the association between production of THFα by tumor or host tissues and malignancy associated hypercalcemia (Calci. Tissue Int. (US) 46(Suppl.), S3–10 (1990)). In Graft versus Host Disease, increased serun TNFα levels have been associated with major complications following acute allogenic bone marrow transplants (Holler et al., Blood, 75(4), 1011–1016 (1990)).

Cerebral malaria is a lethal hyperacute neurological syndrome associated with high blood levels of TNFα and is the most severe complication occurring in malaria patients. Levels of serum TNFα correlated directly with the severity of the disease and the prognosis in patients with acute malaria attacks (Grau et al., N. Engl. J. Med. 320(24), 1586–1591 (1989)).

TNFα also plays a role in the area of chronic pulmonary inflammatory diseases. The deposition of silica particles leads to silicosis, a disease of progressive respiratory failure caused by a fibrotic reaction. Antibodies to TNFα completely blocked the silica-induced lung fibrosis in mice (Pignet et al., Nature, 344:245–247 (1990)). High levels of TNFα production, in the serum and in isolated macrophages, have been demonstrated in animal models of silica and asbestos induced fibrosis (Bissonnette et al., Inflammation 13(3), 329–339 (1989)). Alveolar macrophages from pulmonary sarcoidosis patients have also been found to spontaneously release massive quantities of TNFα as compared with macrophages from normal donors (Baughman et al., J. Lab. Clin. Med. 115(1), 36–42 (1990)).

TNFα is also implicated in the inflammatory response which follows reperfusion, called reperfusion injury, and is a major cause of tissue damage after loss of blood flow (Vedder et al., PNAS 87, 2643–2646 (1990)). TNFα also alters the properties of endothelial cells and has various pro-coagulant activities, such as producing an increase in tissue factor pro-coagulant activity and suppression of the anticoagulant protein C pathway as well as down-regulating the expression of thrombomodulm (Sherry et al., J. Cell Biol. 107, 1269–1277 (1988)). TNFα has pro-inflammatory activities which together with its early production (during the initial stage of an inflammatory event) make it a likely mediator of tissue injury in several important disorders including but not limited to, myocardial infarction, stroke and circulatory shock. Of specific importance may be TNFα-induced expression of adhesion molecules, such as intercellular adhesion molecule (ICAM) or endothelial leukocyte adhesion molecule (ELAM) on endothelial cells (Munro et al., Am. J. Path. 135(1), 121–132 (1989)).

Moreover, it is now known that TNFα is a potent activator of retrovirus replication including activation of HIV-1. (Duh et al., Proc. Nat. Acad. Sci. 86, 5974–5978 (1989); Poll et al., Proc. Nat. Acad. Sci. 87, 782–785 (1990); Monto et al., Blood 79, 2670 (1990); Clouse et al., J. Immunol. 142, 431–438 (1989); Poll et al., AIDS Res. Hum. Retrovirus, 191–197 (1992)). AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1 and HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T lymphocyte activation. Therefore, interference with cytokine activity such as by prevention, control, or inhibition of cytokine production, notably TNFα, in a HIV-infected individual aids in limiting the maintenance of T lymphocyte activation caused by HIV infection.

Monocytes, macrophages, and related cells, such as kupffer and glial cells, have also been implicated in maintenance of the HIV infection. These cells, like T cells, are targets for viral replication and the level of viral replication is dependent upon the activation state of the cells (Rosenberg et al., The Immunopathogenesis of HIV Infection, Advances in Immunology, 57 (1989)). Cytokines, such as TNFα, have been shown to activate HIV replication in monocytes and/or macrophages (Poli et al., Proc. Natl. Acad. Sci., 87, 782–784 (1990)), therefore, prevention, control, or inhibition of cytokine production or activity aids in limiting HIV progression as stated above for T cells. Additional studies have identified TNFα as a common factor in the activation of HIV in vitro and has provided a clear mechanism of action via a nuclear regulatory protein found in the cytoplasm of cells (Osborn, et al., PNAS 86, 2336–2340). This evidence suggests that a reduction of TNFα synthesis may have an antiviral effect in HIV infections, by reducing the transcription and thus virus production.

HIV viral replication of latent HIV in T cell and macrophage lines can be induced by TNFα(Folks et al., *PNAS* 86, 2365–2368 (1989)). A molecular mechanism for the virus inducing activity is suggested by TNFα's ability to activate a gene regulatory protein (NFκB) found in the cytoplasm of cells, which promotes HIV replication through binding to a viral regulatory gene sequence (LTR) (Osborn et al., *PNAS* 86, 2336–2340 (1989)). TNFα in AIDS associated cachexia is suggested by elevated serum TNFα and high levels of spontaneous TNFα production in peripheral blood monocytes from patients (Wright et al. *J. Immunol.* 141(1), 99–104 (1988)).

TNFα has been implicated in various roles with other viral infections, such as the cytomegalia virus (CMV), influenza virus, adenovirus, and the herpes family of viruses for similar reasons as those noted.

Preventing, controlling, or inhibiting the production or action of TNFα (e.g. treatment with the compounds of this invention) is, therefore, predicted to be a potent therapeutic strategy for many inflammatory, infectious, immunological or malignant diseases. These include but are not restricted to septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis, other arthritic conditions, Crohn's disease, ulcerative colitis, multiple sclerosis, systemic lupus erythrematosis, ENL in leprosy, radiation damage, asthma, and hyperoxic alveolar injury. Efforts directed to the suppression of the effects of TNFα have ranged from the utilization of steroids such as dexamethasone and prednisolone to the use of both polyclonal and monoclonal antibodies (Beutler et al., *Science* 234, 470–474 (1985); WO 92/11383).

The nuclear factor κB (NFκB) is a pleiotropic transcriptional activator (Lenardo, et al. *Cell* 1989, 58, 227–29). NFκB has been implicated as a transcriptional activator in a variety of disease and inflammatory states and is thought to regulate cytokine levels including but not limited to TNFα and also to be an activator of HIV transcription (Dbaibo, et al. *J. Biol. Chem.* 1993, 17762–66; Duh et al. *Proc. Natl. Acad. Sci.* 1989, 86, 5974–78; Bachelerie et al. *Nature* 1991, 350, 709–12; Boswas, J. et al. *Acquired Immune Deficiency Syndrome* 1993, 6, 778–786; Suzuki et al. *Biochem. And Biophys. Res. Comm.* 1993, 193, 277–83; Suzuki et al. *Biochem. And Biophys. Res Comm.* 1992, 189, 1709–15; Suzuki et al. *Biochem. Mol. Bio. Int.* 1993, 31(4), 693–700; Shakhov et al. 1990, 171, 35–47; and Staal et al. *Proc. Natl. Acad. Sci. USA* 1990, 87, 9943–47). Thus, inhibition or activation of NFκB binding can regulate transcription of cytokine gene(s) and through this modulation and other mechanisms be useful in the inhibition of a multitude of disease states. The compounds claimed in this patent can inhibit the action of NFκB in the nucleus and thus are useful in the treatment of a variety of diseases including but not limited to asthma, rheumatoid arthritis, rheumatoid spondylitis, osteoarthritis, other arthritic conditions, septic shock, septis, endotoxic shock, graft versus host disease, wasting, Crohn's disease, ulcerative colitis, multiple sclerosis, systemic lupus erythrematosis, ENL in leprosy, HIV, AIDS, and opportunistic infections in AIDS.

TNFα and NFκB levels are influenced by a reciprocal feedback loop. As noted above, the compounds of the present invention affect the levels of both TNFα and NFκB. It is not known at this time, however, how the compounds of the present invention regulate the levels of TNFα, NFκB, or both.

Many cellular functions can be mediated by levels of adenosine 3',5'-cyclic monophosphate(cAMP). Such cellular functions can contribute to inflammatory conditions and diseases including asthma, inflammation, and other conditions (Lowe and Cheng, *Drugs of the Future*, 17(9), 799–807, 1992). It has been shown that the elevation of cAMP in inflammatory leukocytes inhibits their activation and the subsequent release of inflammatory mediators. Increased levels of cAMP also leads to the relaxation of airway smooth muscle.

The primary cellular mechanism for the inactivation of cAMP is the breakdown of cAMP by a family of isoenzymes referred to as cyclic nucleotide phosphodiesterases (PDE) (Beavo and Reitsnyder, *Trends in Pharm.*, 11, 150–155, 1990). There are seven known members of the family of PDEs. It is recognized, for example, that the inhibition of PDE type IV is particularly effective in both the inhibition of inflammatory mediator release and the relaxation of airway smooth muscle (Verghese, et al., *Journal of Pharmacology and Experimental Therapeutics*, 272(3), 1313–1320, 1995). Thus, compounds that inhibit PDE IV specifically, would exhibit the desirable inhibition of inflammation and relaxation of airway smooth muscle with a minimum of unwanted side effects, such as carclio-vascular or anti-platelet effects. Currently used PDE IV inhibitors lack the selective action at acceptable therapeutic doses.

The compounds of the present invention are useful in the inhibition of phosphodiesterases, particularly PDE III and PDE IV, and in the treatment of disease states mediated thereby.

DETAILED DESCRIPTION

The present invention is based on the discovery that a class of non-polypeptide imides more fully described herein appear to inhibit the action of TNFα.

The present invention pertains to compounds of the formula:

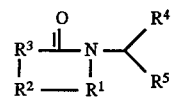

in which:

$R^1$ is —CH$_2$—, —CH$_2$CO—, or —CO—;

$R^2$ and $R^3$ taken together are (i) ethylene unsubstituted or substituted with alkyl of 1–10 carbon atoms or phenyl, (ii) vinylene substituted with two substituents each selected, independently of the other, from the group consisting of alkyl of 1–10 carbon atoms and phenyl, or (iii) a divalent cycloalkyl or bicyclic alkyl of 5–10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl unsubstituted or substituted with alkyl of 1—3 carbon atoms, acetoxy, carboxy, hydroxy, amino, substituted amino, alkyl of 1 to 10 carbon atoms, alkoxy of 1 to 10 carbon atoms, norbornyl, phenyl or halo;

$R^4$ is a (i) straight or branched unsubstituted alkyl of 4 to 8 carbon atoms, (ii) cycloalkyl of 5–10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, branched, straight or cyclic alkyl of 1 to 10 carbon atoms, alkoxy of 1 to 10 carbon atoms, phenyl or halo, (iii) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, cycloalkyl of 3 to 10 carbon atoms, cycloalkoxy of 3 to 10 carbon atoms, phenyl or halo, (iv) heterocycle of 4–10 atoms, including pyridine and pyrrolidine, unsubstituted or substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl or halo;

$R^5$ is —COX, —CN, —CH$_2$COX, alkyl of 1 to 5 carbon atoms, aryl, —CH$_2$OR, —CH$_2$aryl, or —CH$_2$OH,
where X is NH$_2$, OH, NHR, or OR$_6$,
where R is lower alkyl; and,
where R$_6$ is alkyl or benzyl.

The term alkyl as used herein denotes a univalent saturated branched or straight hydrocarbon chain. Unless otherwise stated, such chains can contain from 1 to 18 carbon atoms. Representative of such alkyl groups are methyl, ethyl, propyl, isopropyl, butyl, isobutyl, sec-butyl, tert-butyl, pentyl, isopentyl, neopentyl, tert-pentyl, hexyl, isohexyl, heptyl, octyl, nonyl, decyl, undecyl, dodecyl, tridecyl, tetradecyl, pentadecyl, hexadecyl, heptadecyl, octadecyl, and the like. When qualified by "lower", the alkyl group will contain from 1 to 6 carbon atoms. The same carbon content applies to the parent term "alkane" and to derivative terms such as "alkoxy".

The term cycloalkyl (or cyclic alkyl) as used herein denotes a univalent saturated cyclic or bicyclic hydrocarbon chain. Unless otherwise stated, such chains can contain from 1 to 18 carbon atoms. Representative of such cycloalkyl groups are methyl, ethyl, cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, cyclooctadecyl, cyclic terpenes, and the like. When qualified by "lower", the cycloalkyl group will contain from 3 to 6 carbon atoms. The same carbon content applies to the parent term "cycloalkane" and to derivative terms such as "cycloalkoxy".

Typical compounds of this invention include:
Methyl 3-succinimidyl-(3,4-dimethoxyphenyl)propionate,
Methyl 3-succinimidyl-(3-ethoxy-4-methoxyphenyl)propionate,
Methyl 3-succinimidyl-(3-cyclopentoxy-4-methoxyphenyl)propionate,
Ethyl 3-succinimidyl-(3,4-diethoxyphenyl)propionate,
Methyl 3-succinimidyl-(4-methoxyphenyl)propionate,
Methyl 3-(cis-1,2,5,6-tetrahydrophthalimido)-3-(3,4-dimethoxyphenyl)propionate,
3-(cis-1,2,5,6-tetrahydrophthalimido)-3-(3,4-dimethoxyphenyl)propionamide,
Methyl 3-(cis-1,2,5,6-tetrahydrophthalimido)-3-(3,4-ethoxyphenyl)propionate,
Ethyl 3-(cis-hexahydrophthalimido)-3-(3,4-ethoxyphenyl)propionate,
Propyl 3-(cis-hexahydrophthalimido)-3-(3-cyanophenyl)propionate,
Ethyl 3-(4'-amino-cis-hexahydrophthalimido)-3-(3,4-dimethoxyphenyl)propionate,
3-(4'-amino-cis-hexahydrophthalimido)-3-(3,4-dimethoxyphenyl)propionitrile,
Ethyl 3-maleimido-3-(3,4-diethoxyphenyl)propionate,
3-maleimido-3-(3,4-diethoxyphenyl)propionamide,
Methyl 3-(4-amino-3,4,5,6-tetrahydrophthalimido)-3-(3,4-dimethoxyphenyl)propionate,
Methyl 3-(3-amino-3,4,5,6-tetrahydrophthalimido)-3-(3,4-diethoxyphenyl)propionate,
Methyl 3-(3,4,5,6-tetrahydrophthalimido)-3-(4-methoxyphenyl)propionate,
Methyl 3-(3-amino-3,4,5,6-tetrahydrophthalimido)-3-(3,4-dihydroxyphenyl)propionate, and
3-(3-amino-3,4,5,6 -tetrahydrophthalimido)-3-(3-hydroxyphenyl)propionitrile.

A first preferred subclass pertains to compounds in which $R^4$ is aryl and $R^5$ is CH$_2$CO$_2$CH$_3$, CN, or CH$_2$CONH$_2$.

The compounds can be used, under the supervision of qualified professionals, to inhibit the undesirable effects of TNFα. The compounds can be administered orally, rectally, or parenterally, alone or in combination with other therapeutic agents including antibiotics, steroids, etc., to a mammal in need of treatment. Oral dosage forms include tablets, capsules, dragees, and similar shaped, compressed pharmaceutical forms. Isotonic saline solutions containing 20–100 milligrams/milliliter can be used for parenteral administration which includes intramuscular, intrathecal, intravenous and intra-arterial routes of administration. Rectal administration can be effected through the use of suppositories formulated from conventional carriers such as cocoa butter.

Dosage regimens must be titrated to the particular indication, the age, weight, and general physical condition of the patient, and the response desired, but generally doses will be from about 1 to about 500 milligrams/day as needed in single or multiple daily administration. In general, an initial treatment regimen can be copied from that known to be effective in interfering with TNFα activity for other TNFα mediated disease states by the compounds of the present invention. Treated individuals will be regularly checked for T cell numbers and T4/T8 ratios and/or measures of viremia such as levels of reverse transcriptase or viral proteins, and/or for profession of cytokine-mediated disease associated problems such as cachexia or muscle degeneration. If no effect is seen following the normal treatment regimen, then the amount of cytokine activity interfering agent administered is increased, e.g., by fifty percent a week.

The compounds of the present invention can also be used topically in the treatment or prophylaxis of topical disease states mediated or exacerbated by excessive TNFα production, such as viral infections, for example those caused by the herpes viruses, or viral conjunctivitis, etc.

The compounds can also be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anaemia virus, caprine arthritis virus, visna virus, and maedi virus, as well as other lentiviruses.

Certain of these compounds possess centers of chirality and can exist as optical isomers. Both the racemates of these isomers and the individual isomers themselves, as well as diastereoisomers when there are two chiral centers, are within the scope of the present invention. The racemates can be used as such or can be separated into their individual isomers mechanically as by chromatography using a chiral absorbent. Alternatively, the individual isomers can be prepared in chiral form or separated chemically from a mixture by forming salts with a chiral acid, such as the individual enantiomers of 10-camphorsulfonic acid, camphoric acid, alpha-bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as to obtain either or both substantially free of the other; i.e., in a form having an optical purity of >95%.

Prevention or inhibition of production of TNFα by these compounds can be conveniently assayed using methods known in the art. For example, TNFα Inhibition Assays in LPS stimulated PBMC have been performed as follows:

PBMC isolation:

PBMC from normal donors were obtained by Ficoll-Hypaque density centrifugation. Cells were cultured in RPMI supplemented with 10% AB+ serum, 2 mM L-glutamine, 100 U/mL penicillin and 100 μg/mL streptomycin.

PBMC suspensions:

Drugs were dissolved in DMSO (Sigma Chemical), further dilutions were done in supplemented RPMI. The final DMSO concentration in the presence or absence of drug in the PBMC suspensions was 0.25 wt %. Drugs were assayed at half-log dilutions starting at 50 μg/mL. Drugs were added to PBMC ($10^6$ cells/mL) in 96 wells plates one hour before the addition of LPS.

Cell stimulation:

PBMC ($10^6$ cells/mL) in the presence or absence of drug were stimulated by treatment with 1 μg/mL of LPS from *Salmonella minnesota* R595 (List Biological Labs, Campbell, Calif.). Cells were then incubated at 37° C. for 18–20 hours. Supernatants were then harvested and assayed immediately for TNFα levels or kept frozen at −70° C. (for not more than 4 days) until assayed.

Cytokine Determination:

The concentration of TNFα in the supernatant was determined by human TNFα ELISA kits (ENDOGEN, Boston, Mass.) according to the manufacturer's directions.

The compounds can be prepared using methods which are known in general for the preparation of imides. General reaction schemes are illustrated by the formulas:

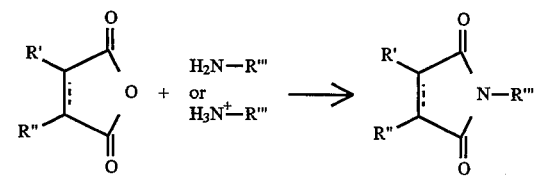

1)

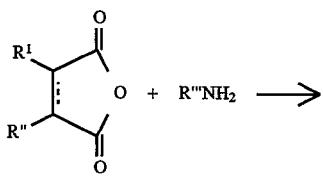

2)

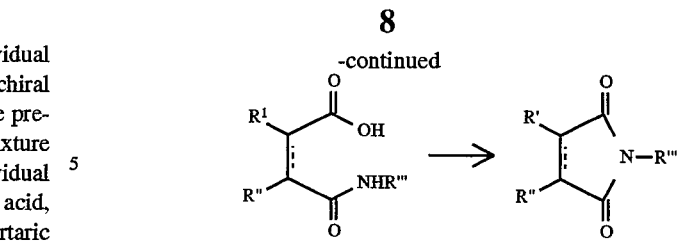

-continued

The following examples will serve to further typify the nature of this invention but should not be construed as a limitation in the scope thereof, which scope is defined solely by the appended claims.

EXAMPLE 1

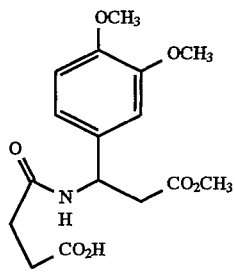

N-[1-(3,4-dimethoxyphenyl)-2-carbomethoxy-methane]-3-carboxypropionamide.

To a suspension of succinic anhydride (0.50 grams, 5.0 mmol) and methyl 3-amino-3-(3,4-dimethoxyphenyl) propionate hydrochloride (1.38 grams, 5.0 mmol) in methylene chloride (20 mL) was added triethylamine (0.75 mL, 5.4 mmol), after 34 minutes the mixture became homogeneous. The solution was stirred at room temperature for 1.5 hours. The progress of the reaction was monitored by TLC (5% methanol/methylene chloride, UV, $I_2$), the product and starting material had similar Rf values but the starting material stained dark yellow with iodine. The solution was washed successively with aqueous 5N hydrochloric acid (15 mL) and water (10 mL). The resulting organic layer was dried over magnesium sulfate and concentrated in vacuo to afford 1.2 grams (70%) of product as a white foam; $^1$H NMR (CDCl$_3$) δ 7.04–6.89 (m, 1H), 6.88–6.72(m, 3H), 5.93–5.25 (m, 1H), 3.85(s, 3H), 3.84(s, 3H), 3.63(s, 3H), 3.01–2.71(m, 2H), 2.76–2.39(m, 4H); $^{13}$C NMR (CDCl$_3$) δ 176.2, 171.8, 171.4, 149.0, 148.5, 132.8, 118.2, 111.2, 109.9, 55.9, 55.8, 51.9, 48.6, 39.8, 30.7, 29.5.

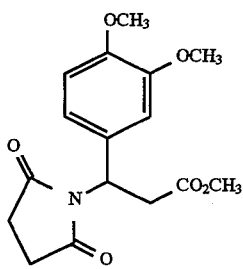

Methyl 3-succinimidyl-(3,4-dimethoxyphenyl)propionate.

A mixture of N-[1-(3,4-dimethoxyphenyl)-2-carbomethoxy-methane]-3-carboxypropionamide (0.61 grams, 1.8 mmol) and sodium acetate (0.07 grams, 0.9 mmol) in acetic anhydride (8 mL) was refluxed for 30 minutes. The progress of the reaction was monitored by TLC (10% methanol/methylene chloride, UV) and had reached

9 completion after 30 minutes. The reaction mixture was cooled to room temperature, poured into iced water (50 mL) and stirred for 15 minutes. The mixture was extracted into ether (25 mL) and was washed successively with a saturated aqueous solution of sodium bicarbonate (25 mL), brine (10 mL), sodium bicarbonate (25 mL) and brine (10 mL). The ether layer was dried over magnesium sulfate and concentrated in vacuo to afford 0.36 grams of crude product as a brown oil. The crude product was purified by flash chromatography (silica gel, 10% ethyl acetate/methylene chloride) to afford 0.23 grams (40%) of product as an oil which solidified to a white solid following refrigeration; $^1$H NMR (CDCl$_3$) δ 7.18–7.01(m, 2H), 6.90–6.74(m, 1H), 5.68–5.54 (m, 1H), 3.88(s, 3H), 3.86(s, 3H), 3.83–3.62(m, 1H), 3.66(s, 3H), 3.22–3.04(m, 1H), 2.65(s, 4H); $^{13}$C NMR (CDCl$_3$) δ 177.1, 171.1, 148.8, 130.5, 111.3, 110.9, 55.9, 55.8, 51.9, 51.4, 34.8, 27.9; Anal. Calcd. for C$_{16}$H$_{19}$NO$_6$. Theoretical: C, 59.81; H, 5.96; N, 4.36. Found: C, 60.00; H, 5.98; N, 4.26.

EXAMPLE 2

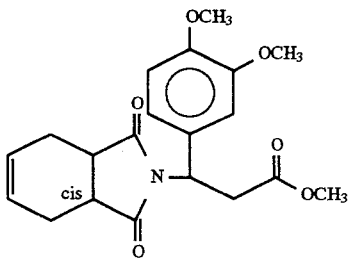

Methyl 3-(cis-1,2,5,6-tetrahydrophthalimido)-3-(3,4-dimethoxyphenyl)propionate.

A stirred mixture of cis-1,2,5,6-tetrahydrophthalic anhydride (0.76 grams, 5.0 mmol), methyl 3-amino-3-(3,4-dimethoxyphenyl)propionate hydrochloride (1.38 grams, 5.0 mmol), and sodium acetate (0.41 grams, 5.0 mmol) in 20 mL of acetic acid under N$_2$ was heated to reflux for 20 hours. The cooled reaction mixture was concentrated in vacuo and the residue diluted with 25 mL of methylene chloride and then 25 mL of saturated sodium bicarbonate was added in portions and the resulting mixture stirred for 30 minutes. The organic phase was separated, dried (sodium sulfate), and concentrated in vacuo to afford the crude product as an oil. The crude product was purified by flash chromatography (silica gel, 1/9 ethyl acetate/hexanes) to afford 0.85 grams (46%) of methyl 3-(cis-1,2,5,6-tetrahydrophthalimido)-3-(3,4-dimethoxyphenyl)-propionate as a solid: mp 100°–101.5° C.; $^1$H NMR (CDCl$_3$/TMS) δ 7.00 (m, 2H), 5.83 (m, 2H), 5.77 (dd, J=10.0, 5.9 Hz, 1H, CH), 3.85 (s, 6H, 2 OCH$_3$), 3.62 (dd, J=10.0, 16.4 Hz, 1H), 3.64 (s, 3H, OCH$_3$), 3.10 (dd, J=16.4, 5.9 Hz, 1H), 3.00 (m, 2H), 2.62–2.45 (m, 2H), 2.30–2.22 (m, 2H); $^{13}$C NMR (CDCl$_3$/TMS) δ 180.0, 179.7, 170.3, 148.8, 130.6, 127.6, 127.5, 120.1, 111.0, 110.8, 55.8, 55.8, 51.8, 51.4, 38.8, 35.3, 23.5, 23.4; TLC (1/9 EtOAc/hexanes, UV) R$_f$=0.34. Anal. Calcd for C$_{20}$H$_{23}$NO$_6$. Theory C, 64.33; H, 6.21; N, 3.75. Found C, 64.29; H, 6.19; N, 3.68.

EXAMPLE 3

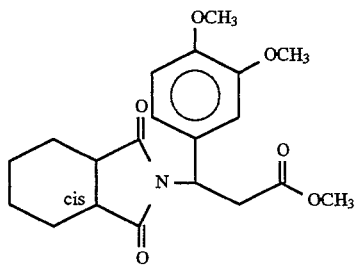

Methyl 3-(cis-hexahydrophthalimido)-3-(3,4-dimethoxyphenyl)propionate.

A stirred mixture of 1,2,5,6-hexahydrophthalic anhydride (0.77 grams, 5.0 mmol), methyl 3-amino-3-(3,4-dimethoxyphenyl)propionate hydrochloride (1.38 grams, 5.0 mmol), and sodium acetate (0.40 grams, 4.9 mmol) in 20 mL of acetic acid under N$_2$ was heated to reflux for 20 hours. The cooled reaction mixture was concentrated in vacuo and the residue diluted with 25 mL of methylene chloride and then 25 mL of sat. sodium bicarbonate was added in portions and the resulting mixture stirred for 30 minutes. The organic phase was separated, dried (sodium sulfate), and concentrated to afford the crude product as an oil. The crude product was purified by flash chromatography (silica gel, 1/9 EtOAc/hexanes) to afford 0.72 grams (38%) of methyl 3-(cis-hexahydrophthalimido)-3-(3,4-dimethoxyphenyl) propionate as an off-white solid (wax): mp 92.5°–95° C.; $^1$H NMR (CDCl$_3$/TMS) δ 7.02 (m, 2H, Ar), 6.65 (m, 1H, Ar), 5.56 (dd, J=5.5, 10.5 Hz, 1H CHN), 3.86 (2 s, 6H, 2 OCH$_3$), 3.74 (dd, J=16.5, 10.5 Hz, 1H), 3.66 (s, 3H, OCH$_3$), 3.08 (dd, J=5.5, 16.5 Hz, 1H, CHCO), 2.77 (m, 2H, bridgehead Hs), 1.87–1.55 (m, 4H), 1.5–1.2 (m, 4H); $^{13}$C NMR (CDCl$_3$/TMS) δ 179.5, 179.4, 171.1, 148.9, 148.8, 130.9, 120.1, 111.0, 110.9, 55.9, 55.8, 51.8, 51.0, 39.6, 35.2, 23.6, 23.5, 21.6; TLC (1/9 EtOAc/hexanes, UV) R$_f$=0.36. Anal. Calcd for C$_{20}$H$_{25}$NO$_6$. Theory C, 63.99; H, 6.71; N, 3.73. Found C, 63.89; H, 6.81; N, 3.61.

EXAMPLE 4

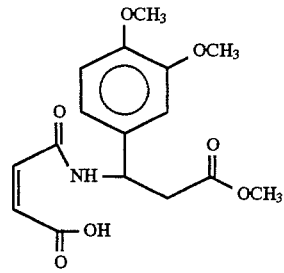

Methyl N-(maleic acid)-3-amino-3-(3',4'-dimethoxyphenyl) propionate.

To stirred suspension of methyl)-3-amino-3-(3',4'-dimethoxyphenyl)propionate hydrochloride (1.38 grams, 5.00 mmol) and maleic anhydride (0.49 grams, 5.0 mmol) in methylene chloride (20 mL) was added 0.75 mL of triethylamine (5.4 mmol). After 1 hour, the reaction mixture was washed with 0.5N hydrochloric acid (15 mL) and water (10 mL). The organic layer was dried (sodium sulfate) and concentrated to yield 1.59 grams (94%) of the product as a white foam: $^1$H NMR (dmso-d$_6$, 250 MHZ) δ 14.27 (br s, 1H), 9.35 (d, J=8.3 Hz, 1H), 7.05–6.80 (m, 3H), 6.38 (d, J=12.4 Hz, 1H), 6.26 (d, J=12.3 Hz, 1),5.23 (m, 1H), 3.76 (s, 3H), 3.73 (s, 3H), 3.57 (s, 3H), 2.85 (m, 2H); $^{13}$C (dmso-d$_6$, 250 MHZ) 170.4, 165.9, 164.2, 148.7, 148.2, 133.2, 132.4, 131.3, 118.6, 111.6, 110.6, 55.5, 51.5, 49.7.

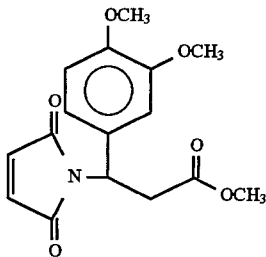

Methyl 3-maleimido-3-(3,4-dimethoxyphenyl)propionate.

A mixture of methyl N-(maleic acid)-3-amino-3-(3',4'-dimethoxyphenyl)propionate (1.0 gram, 1.5 mmol) and sodium acetate (1.48 mmol) in 7.5 mL of acetic anhydride was stirred at room temperature for 2 hours, then heated to reflux for 20 minutes. The cooled (10° C.) reaction mixture was poured into 50 mL of ice water and stirred for 15 minutes and then extracted with 50 mL of diethyl ether. The ether layer was washed successively with sodium bicarbonate (20 mL) and brine (20 mL). The ether layer was dried over sodium sulfate and concentrated in vacuo to afford a light brown oil which was purified by flash chromatography (1/1 ethyl acetate/hexanes, silica gel) to afford 0.47 g (50%) of the product as a wax: mp. 75°–76° C.; $^1$H NMR (dmso-d$_6$, 250 MHZ) δ 7.02 (m, 2H, Ar), 6.80 (m, 1H, Ar), 6.64 (s, 2H, vinyl), 3.87 (s, 3H), 3.85 (s, 3H), 3.7–3.58 (m, 4H, CH, CO$_2$CH$_3$), 3.12 (dd, J=5.8, 16.5 Hz, 1H); $^{13}$C (dmso-d$_6$, 250 MHZ): 170.9, 170.5, 149.0, 148.9, 134.0, 131.0, 120.1, 111.0, 110.9, 55.9, 55.8, 51.9, 50.7, 35.9. Anal. Calcd for C$_{16}$H$_{17}$N$_1$O$_6$. Theoretical: C, 60.18, H, 5.37, N, 4.39. Found: C, 60.18; H, 5.40; N, 4.32.

EXAMPLE 5

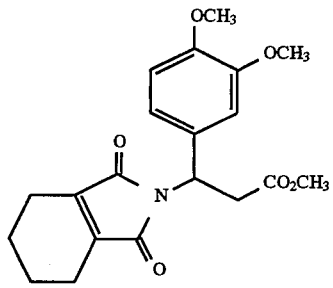

Methyl 3-(3,4,5,6-tetrahydrophthalimido)-3-(3,4-dimethoxyphenyl)propionate.

To a stirred suspension of 3,4,5,6-tetrahydrophthalic anhydride (0.38 grams, 2.5 mmol) and methyl 3-amino-3-(3,4-dimethoxyphenyl)propionate hydrochloride (0.69 grams, 2.5 mmol) in acetic acid (10 mL) was added sodium acetate (0.21 grams, 2.5 mmol). The suspension was refluxed under nitrogen overnight. The acetic acid was removed in vacuo to afford an orange oil which was taken up in water (5 mL) and the pH was adjusted to 7 using a saturated solution of sodium bicarbonate. The resulting mixture was extracted with methylene chloride (3×20 mL). The combined organic extracts were dried over magnesium sulfate, filtered and concentrated in vacuo to afford 0.62 grams of crude product as a yellow oil. The crude product was purified by flash chromatography (silica gel, 35% ethyl acetate/hexane) and the resulting solid was dried in vacuo (60° C., <1 mm) to afford 0.22 g (23%) of product as a pale yellow solid: $^1$H NMR (CDCl$_3$) δ 7.09–6.99(m, 2H), 6.84–6.75(m, 1H), 5.60–5.48(m, 1H), 3.87(s, 3H), 3.85(s, 3H), 3.71–3.55(m, 1H), 3.65(s, 3H), 3.23–3.06(m, 1H), 2.38–2.21(m,4H), 1.85–1.64(m, 4H); $^{13}$C NMR (CDCl$_3$) δ 171.1, 170.8, 148.9, 148.7, 120.1, 111.2, 110.9, 55.9, 55.8, 50.4, 36.1, 21.2, 19.9. Anal. Calcd for C$_{20}$H$_{23}$NO$_6$. Theoretical: C, 64.33; H, 6.21; N, 3.75. Found: C, 64.25; H, 6.10; N, 3.70.

EXAMPLE 6

Tablets, each containing 50 milligrams of active ingredient, can be prepared in the following manner:

| Constituents (for 1000 tablets) | |
| --- | --- |
| active ingredient | 50.0 grams |
| lactose | 50.7 grams |
| wheat starch | 7.5 grams |
| polyethylene glycol 6000 | 5.0 grams |
| talc | 5.0 grams |
| magnesium stearate | 1.8 grams |
| demineralized water | q.s. |

The solid ingredients are first forced through a sieve of 0.6 mm mesh width. The active ingredient, the lactose, the talc, the magnesium stearate and half of the starch are then mixed. The other half of the starch is suspended in 40 milliliters of water and this suspension is added to a boiling solution of the polyethylene glycol in 100 milliliters of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 7

Tablets, each containing 100 milligrams of active ingredient, can be prepared in the following manner:

| Constituents (for 1000 tablets) | |
| --- | --- |
| active ingredient | 100.0 grams |
| lactose | 100.0 grams |
| wheat starch | 47.0 grams |
| magnesium stearate | 3.0 grams |

All the solid ingredients are first forced through a sieve of 0.6 mm mesh width. The active ingredient, the lactose, the magnesium stearate and half of the starch are then mixed. The other half of the starch is suspended in 40 milliliters of water and this suspension is added to 100 milliliters of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 8

Tablets for chewing, each containing 75 milligrams of active ingredient, can be prepared in the following manner:

| Composition (for 1000 tablets) | |
|---|---|
| active ingredient | 75.0 grams |
| mannitol | 230.0 grams |
| lactose | 150.0 grams |
| talc | 21.0 grams |
| glycine | 12.5 grams |
| stearic acid | 10.0 grams |
| saccharin | 1.5 grams |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. The active ingredient, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

EXAMPLE 10

Tablets, each containing 10 milligrams of active ingredient, cart be prepared in the following manner:

| Composition (for 1000 tablets) | |
|---|---|
| active ingredient | 10.0 grams |
| lactose | 328.5 grams |
| corn starch | 17.5 grams |
| polyethylene glycol 6000 | 5.0 grams |
| talc | 25.0 grams |
| magnesium stearate | 4.0 grams |
| demineralized water | q.s. |

The solid ingredients are first forced through a sieve of 0.6 mm mesh width. Then the active ingredient, lactose, talc, magnesium stearate and half of the starch are intimately mixed. The other half of the starch is suspended in 65 milliliters of water and this suspension is added to a boiling solution of the polyethylene glycol in 260 milliliters of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 10

Gelatin dry-filled capsules, each containing 100 milligrams of active ingredient, can be prepared in the following manner:

| Composition (for 1000 capsules) | |
|---|---|
| active ingredient | 100.0 grams |
| microcrystalline cellulose | 30.0 grams |
| sodium lauryl sulphate | 2.0 grams |
| magnesium stearate | 8.0 grams |

The sodium lauryl sulphate is sieved into the active ingredient through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 milligrams each into size 0 (elongated) gelatin dry-fill capsules.

EXAMPLE 11

A 0.2% injection or infusion solution or suspension can be prepared, for example, in the following manner:

| active ingredient | 5.0 grams |
|---|---|
| sodium chloride | 22.5 grams |
| phosphate buffer pH 7.4 | 300.0 grams |
| demineralized water | to 2500.0 milliliters |

The active ingredient is dissolved in 1000 milliliters of water and filtered through a microfilter or slurried in 1000 milliliters of water. The buffer solution is added and the whole is made up to 2500 milliliters with water. To prepare dosage unit forms, portions of 1.0 or 2.5 milliliters each are introduced into glass ampules (each containing respectively 2.0 or 5.0 milligrams of active ingredient).

What is claimed is:

1. A compound having the formula:

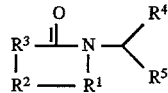

in which:

$R^1$ is —$CH_2$—, —$CH_2CO$—, or —CO—;

$R^2$ and $R^3$ taken together are (i) ethylene unsubstituted or substituted with alkyl of 1–10 carbon atoms or phenyl, (ii) vinylene substituted with two substituents each selected, independently of the other, from the group consisting of alkyl of 1–10 carbon atoms and phenyl, or (iii) a divalent cycloalkyl of 5–10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl unsubstituted or substituted with alkyl of 1–3 carbon atoms, acetoxy, carboxy, hydroxy, amino, substituted amino, alkyl of 1 to 10 carbon atoms, alkoxy of 1 to 10 carbon atoms, norbornyl, phenyl or halo;

$R^4$ is (i) straight or branched unsubstituted alkyl of 4 to 8 carbon atoms, (ii) cycloalkyl or bicycloalkyl of 5–10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, branched, straight or cyclic alkyl of 1 to 10 carbon atoms, alkoxy of 1 to 10 carbon atoms, phenyl or halo, (iii) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, cycloalkyl or bicycloalkyl of 3 to 10 carbon atoms, cycloalkoxy or bicycloalkoxy of 3 to 10 carbon atoms, phenyl or halo, (iv) pyridine or pyrrolidine, unsubstituted or substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl or halo; and, $R^5$ is —COX, —CN, —$CH_2$COX, alkyl of 1 to 5 carbon atoms, aryl, —$CH_2$OR, —$CH_2$aryl, or —$CH_2$OH, where X is $NH_2$, OH, NHR, or $OR_6$, where R is lower alkyl; and, where $P_6$ is alkyl or benzyl.

2. The compound of claim 1 wherein $R^2$ and $R^3$ taken together are cyclohexenyl.

3. The compound of claim 2 wherein the cyclohexenyl is substituted.

4. The compound of claim 1 wherein $R^2$ and $R^3$ taken together are cyclohexyl.

5. The compound of claim 1 wherein $R^2$ and $R^3$ taken together are ethylene.

6. The compound of claim 1 wherein $R^2$ and $R^3$ taken together are vinylene.

7. The compound of claim 6 wherein $R^2$ and $R^3$ are each substituted with phenyl.

8. The compound of claim 6 wherein $R^2$ and $R^3$ are each substituted with methyl.

9. The compound of claim 1 wherein $R^2$ and $R^3$ taken together are cyclopentyl.

10. The method of reducing levels of TNFα in a mammal which administering thereto an effective amount of a compound of the formula:

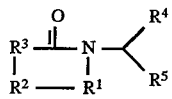

in which:

$R^1$ is —$CH_2$—, —$CH_2$CO—, or —CO—;

$R^2$ and $R^3$ taken together are (i) ethylene unsubstituted or substituted with alkyl of 1–10 carbon atoms or phenyl, (ii) vinylene substituted with two substituents each selected, independently of the other, from the group consisting of alkyl of 1–10 carbon atoms and phenyl, or (iii) a divalent cycloalkyl of 5–10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl unsubstituted or substituted with alkyl of 1–3 carbon atoms, acetoxy, carboxy, hydroxy, amino, substituted amino, alkyl of 1 to 10 carbon atoms, alkoxy of 1 to 10 carbon atoms, norbornyl, phenyl or halo;

$R^4$ is (i) straight or branched unsubstituted alkyl of 4 to 8 carbon atoms, (ii) cycloalkyl or bicycloalkyl of 5–10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, branched, straight or cyclic alkyl of 1 to 10 carbon atoms, alkoxy of 1 to 10 carbon atoms, phenyl or halo, (iii) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, cycloalkyl or bicycloalkyl of 3 to 10 carbon atoms, cycloalkoxy or bicycloalkoxy of 3 to 10 carbon atoms, phenyl or halo, (iv) pyridine or pyrrolidine, unsubstituted or substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl or halo; and, $R^5$ is —COX, —CN, —$CH_2$COX, alkyl of 1 to 5 carbon atoms, aryl, —$CH_2$OR, —$CH_2$aryl, or —$CH_2$OH, where X is $NH_2$, OH, NHR, or $OR_6$, where R is lower alkyl; and, where $R_6$ is alkyl or benzyl.

11. The method of inhibiting TNFα-activated retrovirus replication in a mammal which comprises administering thereto an effective mount of a compound according to claim 1.

12. The method of inhibiting TNFα-activated retrovirus replication in a mammal which comprises administering thereto an effective amount of a compound according to claim 6.

13. A pharmaceutical composition comprising a pharmaceutically acceptable carrier and an amount of a compound according to claim 1 effective upon single or multiple dosage to inhibit TNFα.

14. A pharmaceutical composition comprising a pharmaceutically acceptable carrier and an amount of a compound according to claim 6 effective upon single or multiple dosage to inhibit TNFα.

15. The method of inhibiting phosphodiesterase in a mammal which comprises administering thereto an effective amount of a compound of claim 1.

16. A pharmaceutical composition comprising a pharmaceutically acceptable carrier and an amount of a compound according to claim 1 effective upon single or multiple dosage to inhibit phosphodiesterase.

17. The compound of claim 1 wherein $R^4$ is 3,4-disubstituted phenyl.

18. The compound of claim 1 wherein $R^1$ is —CO—, $R^2$ and $R^3$ taken together are cyclohexyl, $R^4$ is 3,4-dialkoxy substituted phenyl, and $R^5$ is —$CH_2$OX where X is alkoxy.

* * * * *